United States Patent [19]

White

[11] Patent Number: 4,578,485

[45] Date of Patent: Mar. 25, 1986

[54] SYNTHESIS OF SPECTINOMYCIN ANALOGS BY AN IMPROVED GRIGNARD PROCESS

[75] Inventor: David R. White, Kalamazoo, Mich.

[73] Assignee: The Upjohn Company, Kalamazoo, Mich.

[21] Appl. No.: 577,641

[22] Filed: Feb. 8, 1984

[51] Int. Cl.$^4$ .......................................... C07D 323/04
[52] U.S. Cl. .................................................. 549/361
[58] Field of Search ........................................ 549/361

[56] References Cited

U.S. PATENT DOCUMENTS

| | | | |
|---|---|---|---|
| 3,234,092 | 2/1956 | Bergy et al. | 167/65 |
| 4,173,647 | 11/1979 | Maier et al. | 424/283 |
| 4,351,771 | 9/1982 | White et al. | 549/361 |
| 4,380,651 | 4/1983 | White | 549/361 |
| 4,380,652 | 4/1983 | White | 549/361 |
| 4,420,623 | 12/1983 | White | 549/361 |
| 4,532,336 | 7/1985 | White | 549/361 |

OTHER PUBLICATIONS

Boissonnas, Adv. Org. Chem. 3, 159, (1963).
Windholz, et al., Tetrahedron Letters, No. 27, 2555, (1967).
Danishefsky, "Siloxy Dienes in Total Synthesis", Accounts of Chemical Research, vol. 14, pp. 400–406, (1981).
Greene, T. W., Protective Groups in Organic Synthesis, Wiley (1981).
McOmie, J. F., Protective Groups in Organic Chemistry, Plenum Press (1973).

*Primary Examiner*—Ethel G. Love
*Attorney, Agent, or Firm*—Joan Thierstein; Paul J. Koivuniemi

[57] ABSTRACT

The invention concerns a method for the synthesis of 6'-ethyl spectinomycin and analogs thereof, including intermediates utilized in the method. The method comprises converting an enamine by a Grignard addition to various novel dienones not hitherto known. The dienones are then hydrogenated and deblocked to obtain 6'-ethyl spectinomycin and analogs thereof. The 6'-ethyl spectinomycin and analogs thereof prepared by the invention exhibit especially good antibacterial activity.

12 Claims, No Drawings

SYNTHESIS OF SPECTINOMYCIN ANALOGS BY AN IMPROVED GRIGNARD PROCESS

FIELD OF THE INVENTION

The invention concerns a method for the synthesis of 6'-ethyl spectinomycin and analogs thereof, including novel intermediates utilized in the method. The 6'-ethyl spectinomycin and analogs prepared by the invention process exhibit good antibacterial activity.

BACKGROUND OF THE INVENTION

Spectinomycin is a known antibiotic having the formula X. The numbering of carbon atoms for the ring system of spectinomycin; as also used hereinafter for analogs thereof, is as shown. Spectinomycin was first prepared in a microbiological process. See Bergy, et al., U.S. Pat. No. 3,234,092.

Presently, many analogs of spectinomycin are known which exhibit desirable biological activity. Further, several chemical processes and intermediates are known for the preparation of spectinomycin and its various analogs. Those which are believed to be the closest to the present process and novel intermediates therein are summarized in the following two paragraphs.

Preparation of an enamine having formula I wherein $R_1$ and $R_2$ are the same and are blocking groups, and $R_3$ is acyl which is used as a starting material in the present invention is described in U.S. application Ser. No. 449,304 filed Dec. 13, 1982, now U.S. Pat. No. 4,532,336 which is a Continuation-in-part of U.S. application Ser. No. 359,723 filed Mar. 19, 1982, now abandoned. The preparation is also disclosed in U.S. Pat. No. 4,380,651 filed July 20, 1981, U.S. Pat. No. 4,380,652 filed July 20, 1981, and U.S. Pat. No. 4,420,623 filed Mar. 17, 1982. Enoneacylates used to prepare the enamines (I) are described in U.S. Pat. No. 4,351,771. Therefore, U.S. Pat. Nos. 4,380,651, 4,380,652, 4,420,623 and 4,351,771 are incorporated by reference.

Further, U.S. application Ser. No. 449,304 discloses a process by which a dienone is converted to a large variety of 6'-alkylspectinomycin analogs of similar scope as now disclosed for the 6'-ethylspectinomycin and analogs thereof prepared by the present invention process. The process of U.S. application Ser. No. 449,304 is a copper catalyzed Grignard addition.

The present invention provides an improved Grignard process having novel intermediates. The novel intermediates are dienones having formula II wherein $R_1$ and $R_2$ are as described above; and R' is alkyl of from 1-18 carbon atoms, inclusive, which are not disclosed and are not obvious from those previously disclosed in the Grignard process of U.S. Ser. No. 449,304. Further, no low temperature reactions are required in the present process which, furthermore, provides improved yields.

SUMMARY OF THE INVENTION

An enamine is converted by a Grignard addition to various novel dienones not hitherto known. The dienones are then hydrogenated and deblocked to obtain 6'-ethylspectinomycin and analogs thereof.

DETAILED DESCRIPTION OF THE INVENTION

The present embodiment includes:
A compound having the formula II wherein
$R_1$ and $R_2$ are the same and are a blocking group; and
R' is alkyl of from 1 to 18 carbon atoms, inclusive;
and further the embodiment herein is:

(A) A process as shown in Scheme A for preparing a compound having the formula III wherein R' is alkyl of from 1 to 18 carbon atoms, inclusive; and
$R_4$ is hydrogen or a blocking group, which comprises
(1) hydrogenating a compound having the formula II wherein $R_1$ and $R_2$ are blocking groups; and
R' is as defined above to obtain the compound III with the proviso that $R_4$ is hydrogen if the blocking groups are removed by the hydrogenation and $R_4$ is a blocking group if the blocking groups $R_1$ and $R_2$ are not removed by the hydrogenation; or
which comprises (2) hydrogenating a compound having the formula II as defined in (A) above with the proviso that $R_1$ and $R_2$ are blocking groups not removed by the hydrogenation and removing the blocking groups to obtain the compound of formula III wherein $R_4$ is hydrogen; and (B) A process of Scheme B for preparing a compound having the formula II wherein $R_1$ and $R_2$ are the same and are a blocking group; and
R' is alkyl of from 1 to 18 carbon atoms, inclusive; which comprises
(a) stirring an enamine having the formula I wherein
$R_1$ and $R_2$ are as defined above; and
$R_3$ is acyl;
with a silylating reagent;
(b) treating the product of step (1) with a compound having the formula R' MgHal wherein R' is as defined above; and
(c) removing the silicon containing protective group to obtain the compound II by treating, the product of step (2) with, for example, hydrogen fluoride; and (C) A process of Scheme C for preparing a compound having the formula III wherein
$R_4$ is hydrogen or a blocking group;
R' is alkyl of from 1 to 18 carbon atoms, inclusive; which comprises combining the steps of Scheme B and Scheme A, i.e., in the following order (a), (b), (c), (1), (2) or (3).

The products of each of the steps may or may not be isolated. The product of step (a) of Scheme B may be advantageously concentrated before continuing with step (b). The product of Scheme B may be removed from the reaction mixture by conventional methods for further treatment.

More specifically the alkyl of from 1 to 18 carbon atoms, inclusive, may be a straight or branched chain or a cyclic group.

It is a preferred embodiment that if R' is a branched chain or cyclic group the longest extension of the branched chain or cyclic group contains from 1 to 4 carbon atoms, inclusive.

The embodiment is a compound prepared by the above process which is 6'-n-propylspectinomycin, 6'-n-butylspectinomycin or 6'-n-pentylspectinomycin.

Further examples of alkyl of from 1 to 18 may be methyl, ethyl, isopropyl, isobutyl, t-butyl, and the like; or 3,3-dimethyl-n-butyl, and the like; cyclopentyl, cyclohexyl, and the like; and 3-methylcyclopentyl, 2-ethylcyclohexyl, and the like.

Blocking groups referred to above on the nitrogen of the C-1 and C-3 substituents and denoted as $R_1$, $R_2$ or $R_4$ are sometimes called "protecting groups" in the art and are well known in many fields of organic chemistry, including peptide chemistry, fatty acid chemistry and especially semi-synthetic and synthetic antibiotic chemistry. Three commonly used blocking groups are halogenated alkoxycarbonyl, aralkoxycarbonyl, and alkoxycarbonyl. Such groups can be removed easily and replaced by hydrogen atoms with suitable treatments. The treatments may be referred to as deblocking and may vary in detail depending on the particular blocking group and the particular molecule to which it is bonded, with acids or by reduction, etc.

The hydrogenation conditions of step (1) in Scheme A and C and discussed above which reduce the double bond between the C-4' and C-5' of the compound of formula II may effect the deblocking treatment for selected blocking groups included in the definitions of $R_1$ and $R_2$ with hydrogen. However, other blocking groups also within the definition of $R_1$ and $R_2$ may require deblocking treatment using different hydrogenation conditions from those of step (1) in Schemes A and C. On the other hand use of hydrogenation conditions may not result in deblocking for even another select group of blocking groups useful as $R_1$ and $R_2$ of the present invention. In this case, other treatment conditions which are well known in the art easily accomplish the deblocking as taught for compounds in the present invention. Finally, deblocking treatment may be applied to compounds of formula II before hydrogenation thereof. It may also be advantageous to effect hydrogenation and deblocking coincidentally when each is exclusively effective. The deblocking treatments required for each of the above blocking groups and variations thereof will be immediately evident to one of ordinary skill in the art. A discussion regarding various deblocking conditions are also found in McOmie and Greene as cited below.

A quite comprehensive list of blocking groups which can be attached to spectinomycin analogs is also disclosed in U.S. Pat. No. 4,173,647, the selection, preparation, use and removal of which is incorporated herein by reference. Regarding the chemistry of adding and removing such blocking groups, see, for example, Boissonas, Adv. Org. Chem. 3, 159 (1963) and Windholz, et al., Tetrahedron Letters 8, 2555 (1967).

Blocking groups commonly known in the art are aralkoxycarbonyl, halogenated alkoxycarbonyl and alkoxycarbonyl.

Hal means bromo, iodo, or chloro.

Acyl means acetyl, propionyl, isopropionyl, butyryl, sec-butyryl, t-butyryl, and the like.

Halogenated alkoxycarbonyl means mono-, di-, trihalomethoxycarbonyl; mono-, di-, tri-haloethoxycarbonyl; mono-, di-, tri-halopropoxycarbonyl; mono-, di-, tri-halobutoxycarbonyl; mono-, di- tri-halopentoxycarbonyl and isomeric forms thereof.

Aralkoxycarbonyl means benzyloxycarbonyl, phenylthioxycarbonyl, phenylpropoxycarbonyl, diphenyloctoxycarbonyl and isomeric forms thereof and fluoroenylmethoxycarbonyl.

Alkoxycarbonyl means isopropyloxycarbonyl, tertiary-butyloxycarbonyl and tertiary-pentyloxycarbonyl.

Silylating reagents which provide silicon containing protecting groups as referred to above are selected from a variety known in the practice of synthetic organic chemistry, including reactions of various dienes with suitable dienophiles, for example, as reviewed by Danishefsky, "Siloxy Dienes in Total Synthesis", Accounts of Chemical Research, vol. 14, pp. 400–6 (1981). Both the silylating reagents for silicon containing protecting groups and other appropriate oxygen protecting groups for use in the present invention, for example, those equivalent to the acyl which is shown as the definition of $R_3$ above, are discussed in references as follows:

Greene, T. W. *Protective Groups in Organic Synthesis,* Wiley (1981).

McOmie, J. F. *Protective Groups in Organic Chemistry,* Plenum Press (1973),

Silicon containing protecting groups are $R_5$ and $R_6$ in the novel intermediates Ia of the above processes. The silicon containing protecting groups are preferably selected from those known, such as butyldiphenylsilyl, t-butyldimethylsilyl, and trimethylsilyl. Trimethylsilyl is most preferred as $R_5$ and $R_6$ in the novel intermediates shown as Ia.

All of the imtermediates of the present invention which contain one or more oxygen protecting groups are useful intermediates in processes for making succesive intermediates in the present process for making C-6'-ethyl spectinomycin and analogs thereof of the present invention which contain blocking groups on the nitrogen atoms bonded to C-1 and C-3. Replacement of the blocking groups by hydrogen on the nitrogen atoms bonded to C-1 and C-3 in C-6' ethyl spectinomycin and analogs thereof of the invention process provides C-6' analogs of spectinomycin having the formula III which are useful as antimicrobial agents.

Generally, an enamine of formula I is stirred with a silylating medium such as trimethylsilylchloride and hexamethyldisilazane (TMSCl-HMDS) in a solvent such as tetrahydrofuran, dimethoxyethane, or methylene chloride for several hours at about 0° to 80° C. preferably about 55° C. The silylating medium preferred is a one-to-one mixture of hexamethyldisilazane and trimethylsilylchloride. To the product Ia now having silicon containing protective groups on the hydroxy substituents at the C-2 and C-6 positions is added the compound of formula R'MgHal. This addition produces the dienone having formula II and is generally carried out in a conventional manner for Grignard reactions, e.g., in an anhydrous aprotic medium, preferably toluene, benzene or tetrahydrofuran or a mixture of one or more of these. The anhydrous aprotic medium most preferred is a nonpolar solvent such as toluene and benzene. The reaction is generally carried out at a temperature of −20° C. to +100° C., preferably −10° C. to 70° C. Thin layer chromatography indicates complete conversion to disilylated dienone having a formula II wherein the hydroxy substituents are protected by silicon containing protective groups. Aqueous hydrogen fluoride is added to remove the silicon containing protective groups. The crude dienones having formula II may be purified by adsorption on wet packed silica gel followed by elution with trichloromethane, a mixture of acetonitrile and trichloromethane in varying proportions.

The dienone II is hydrogenated by adding hydrogen to the dienone II in the presence of a palladium/barium sulfate catalyst. Suitable solvents for the hydrogenation reaction are 2-propanol, ethanol, or methanol. The presence of pyridine enhances the desired reaction. The hydrogenation is sensitive to stirring efficiency so variations in scale influence the usual variables requiring adjustment within ordinary experimentation. The temperature of the hydrogenation may be −30° C. to 80° C. and is preferable near 25° C.

As discussed above, the removal of the blocking groups; variously $R_1$ and $R_2$ or $R_4$, is carried out before, after or coincidentally with hydrogenation of the dienone II. See steps (1), (2) and (3) above. Note, coincidental deblocking and hydrogenation may also be read as included in step (2) of Schemes A and C such that in addition to hydrogenating conditions, deblocking conditions may be accomplished either consecutively or coincidentally therewith, even if hydrogenation does not deblock at the same time. That is, hydrogenating and deblocking of step (2) may be either consecutive or coincidental. If consecutive either deblocking or hydrogenating can be effected first.

Each of the products prepared in the above steps may be removed from the reaction mixture by conventional methods.

Any method within the skill in the art may be used for isolation of a compound having formula III and methods disclosed herein are not meant to be limiting.

The crude compounds of formula III may be purified by adsorption on a column of a weakly acidic ion exchange resin such as Amberlite IRC-50 or CG-50 followed by elution with a solvent such as water, methanol, ethanol, ether, tetrahydrofuran, 1,2-dimethoxy ethane or p-dioxane containing hydrochloric acid, hydrobromic acid, hydroiodic acid and sulfuric acid.

Acid salts can be made by neutralizing compounds of Formula III with the appropriate acid to below about pH 7.0 and advantageously to about pH 2 to pH 3. Suitable acids for this purpose produce pharmacologically acceptable salts and include hydrochloric, sulfuric, phosphoric, sulfamic, hydrobromic and the like. Acid and base salts of the compounds can be used for the same biological purposes as the parent compound.

The compounds of formula III in the present invention have a utility now well known for spectinomycin and its analogs.

The compounds of formula III are shown to be particularly effective for treating bacterial infection, such as gonorrhea in mammals, including humans. Utility for the compounds of formula III are particularly shown in U.S. application Ser. No. 449,304 now pending and which is hereby incorporated by reference.

The compositions of the present invention are presented for administration to humans and animals in unit dosage forms, such as sterile parenteral solutions or suspensions, eye drops and water-in-oil emulsions containing suitable quantities of the compoud of formula I.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspension can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include, for example, the route of administration and the potency of the particular compound. A dosage schedule for humans of from about 2 to about 4000 mg of compound in a single dose, administered parenterally or in the compositions of this invention, are effective for bacterial infections. More specifically, the single dose is from 5 mg to about 200 mg of compound.

The following Preparation and Example describe the preparation of an analog of spectinomycin and intermediates useful in the preparation thereof which are indicative of the embodiment of this invention but are not to be construed as limitative. Those skilled in the art will promptly recognize variations from the procedures both in the analogs and analog precursors within the novel compounds described as well as reaction conditions and techniques of the invention process.

For example, for each of the Preparation and Example as follows, corresponding 6'-analogs of spectinomycin for each product are contemplated which are within the scope of the invention. That is, the Examples are not meant to be limiting but merely serve to illustrate an embodiment of the present invention.

PREPARATION I

Dienone having the formula II wherein $R_1$ and $R_2$ are benzyloxycarbonyl and $R'$ is ethyl.

Dried enamine having the formula I wherein $R_1$ and $R_2$ are benzyloxycarbonyl and $R_3$ is acetyl (5.00 g) is dissolved in tetrahydrofuran (50 ml). Hexamethyldisilazane (10 ml) and trimethylsilylchloride (10 ml) are added and the solution is stirred at 55° C. for 2.5 hours. Thin layer chromatography of a dried probe in 1:4 $CH_3CN$—$CHCl_3$ shows complete conversion to product, Rf=0.33. The solution is poured into toluene (125 ml), filtered and concentrated to a foam (6.12 g). The material is dissolved in toluene (150 ml) in a 250 ml neck flask equipped with a septum, a stir bar and an $N_2$ inlet. After cooling to 0° C., ethylmagnesium bromide (2.9M in $Et_2O$, 12.0 ml) is added over 5 minutes. After addition, the solution is allowed to come to room temperature. After 1.5 hours thin layer chromatography shows complete conversion to a less polar, disilylated dienone having the formula IIa wherein $R_1$ and $R_2$ are benzyoxycarbonyl; $R_3$ is acetyl; and $R_5$ and $R_6$ are silicon containing protective groups (5:95 $CH_3OH$—$CHCl_3$, Rf=0.56; 1:4 CH₃CN—CHCl₃, Rf=0.91). The mixture is poured onto a solution of EtOAc (150 ml), HOAc (6.0 ml) and saturated NaCl (50 ml). Phases are separated. The aqueous phase is washed with EtOAc (50 ml). Combined organics are dried and concentrated. The foam is dissolved in acetonitrite (75 ml) and cooled to 0° C. 48% aqueous HF (7.5 ml) is added and the solution stirred at 0° C. for 5 hours. Thin layer chromatography shows desilylation (1:4 CH₃CN—CHCl₃, Rf=0.28). The solution is poured onto a mixture of saturated brine (150 ml), EtOAc (100 ml)-toluene (50 ml) mixture. The organic extracts are dried over Na₂SO₄ and concentrated. A coarse sintered glass funnel is wet packed with silica gel (100 ml) and a compound having the formula II wherein R₁ and R₂ are benzyloxycarbonyl is applied as a solution in CHCl₃. It is eluted with CHCl₃ (200 ml), 5:95 CH₃CN—CHCl₃ (200 ml), 1:9 CH₃CN—CHCl₃ (200 ml), 1:4 CH₃CN—CHCl₃ (250 ml) and 1:1 CH₃CN—CHCl₃ (250 ml).

Pure fractions are combined and concentrated to obtain 2.70 g, 59.6% yield of the compound of formula II wherein R₁ and R₂ are benzyloxycarbonyl and R' is ethyl from enamine, the compound of formula I wherein R₁ and R₂ are benzyloxycarbonyl and R₃ is acetyl.

CMR (CD₃COCD₃): 12.6, 26.3, 31.5, 31.7, 57.3, 60.1, 65.2, 66.3, 67.3, 74.6, 76.3, 88.1, 99.1, 101.3, 123.5, 128.3, 128.7, 129.1, 137.7, 145.8, 188.4 ppm.

Utilizing a procedure similar to that used in Preparation 1 but substituting the appropriately substituted 6'-alkyl magnesium halide for ethyl magnesium bromide there is obtained a dienone having the formula II wherein R₁ and R₂ are a blocking group as may be variously found on the enamines I disclosed as starting materials above; and R' is methyl, ethyl, n-butyl, isobutyl, n-pentyl, 3,3-methyl-n-butyl, cyclopentylmethyl, cyclohexylmethyl, n-undecyl, or n-octyl.

EXAMPLE 1

6'-n-Propylspectinomycin having the formula III wherein R' is ethyl.

Three identical reactions are set up as follows: A solution of dienone (0.20 g) in 2-propanol (16.0 ml) is placed in a 50 ml 14/20 neck flask. Pyridine (0.20 ml) and 10% palladium/BaSO₄ (Fluka, brown catalyst, 0.20 g) is added. The flask is equipped with a 1" football stirrer and a septum. The mixture is hydrogenated at 1 atmosphere with efficient stirring. After 2 hours and 20 minutes, thin layer chromatography (CH₃OH—CHCl₃—NH₄OH, 8:6:4) shows complete conversion to product (Rf=0.65). The 3 reactions are filtered together; the filtrate concentrated at 26° C. under high vacuum. The residue is dissolved in water (10 ml), 1M H₂SO₄ (0.93 ml) is added, the mixture filtered and the filtrate lyophilized. The solid is dissolved in water (5.0 ml), acetone is added (5.0 ml) and the solution cooled to 0° C. and seeded.

Additional acetone (5.0 ml) is added while stirring at 0° C. The crystals are filtered, dried at 55° C. under N₂ stream overnight. Then it is placed in 53% relative humidity for 5 days. A yield of 0.32 g (59.4%) of 6'-n-propylspectinomycin having formula III wherein R' is ethyl is obtained.

CMR (D₂O, CH₃CN as IS): 12.4, 21.1, 25.7, 29.7, 30.3, 32.7, 38.7, 57.7, 59.1, 60.8, 64.7, 65.1, 69.0, 71.8, 91.1, 92.8 ppm.

Utilizing a procedure similar to that used in Preparation 1 and Example 1 but substituting the appropriately substituted alkyl magnesium halide for ethyl magnesium bromide in Preparation 1 there is obtained:

6'-ethylspectinomycin,
6'-n-butylspectinomycin,
6'-iso-butylspectinomycin,
6'-n-pentylspectinomycin,
6'-(3,3-dimethyl)-n-butylspectinomycin,
6'-cyclopentylmethylspectinomycin,
6'-cyclohexylmethylspectinomycin,
6'-n-undecylspectinomycin,
6'-n-octylspectinomycin.

FORMULAE

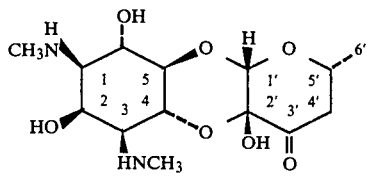

X

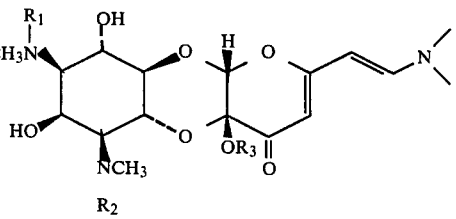

I

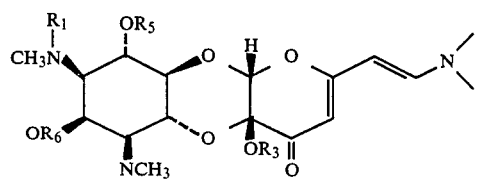

Ia

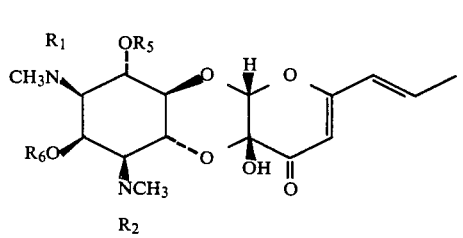

IIa

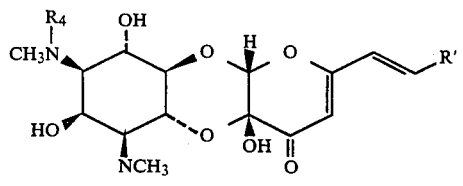

IIb

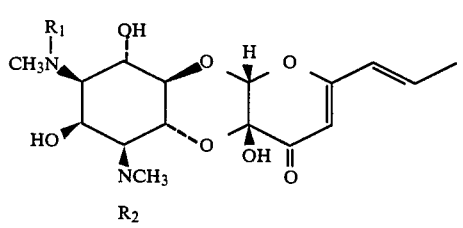

II

-continued
III 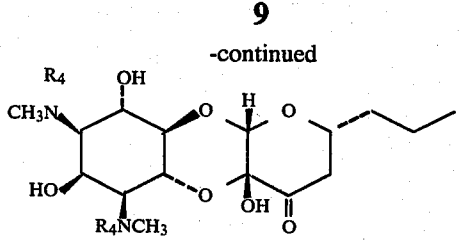
SCHEME B
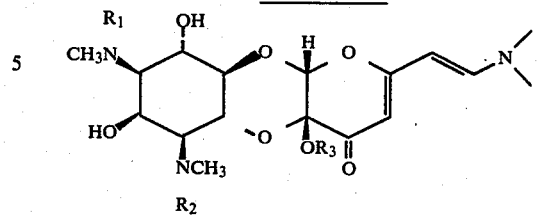
(a) silylating reagent
(b) R'MgHal
(c) HF
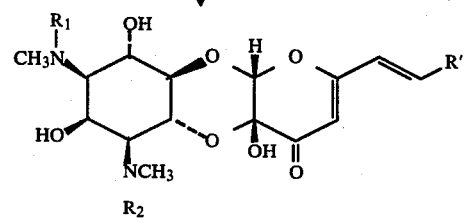 II
SCHEME A
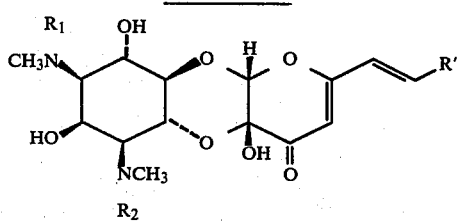 II
(1) hydrogenation
(2) hydrogenating and removing the blocking groups; or
(3) removing the blocking groups and hydrogenating
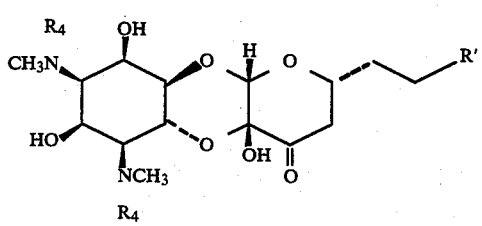
III
wherein $R_4$ is hydrogen or a blocking group
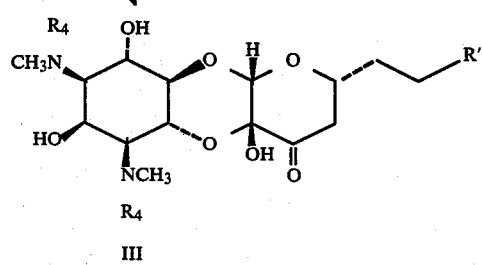
III
wherein $R_4$ is hydrogen SCHEME C
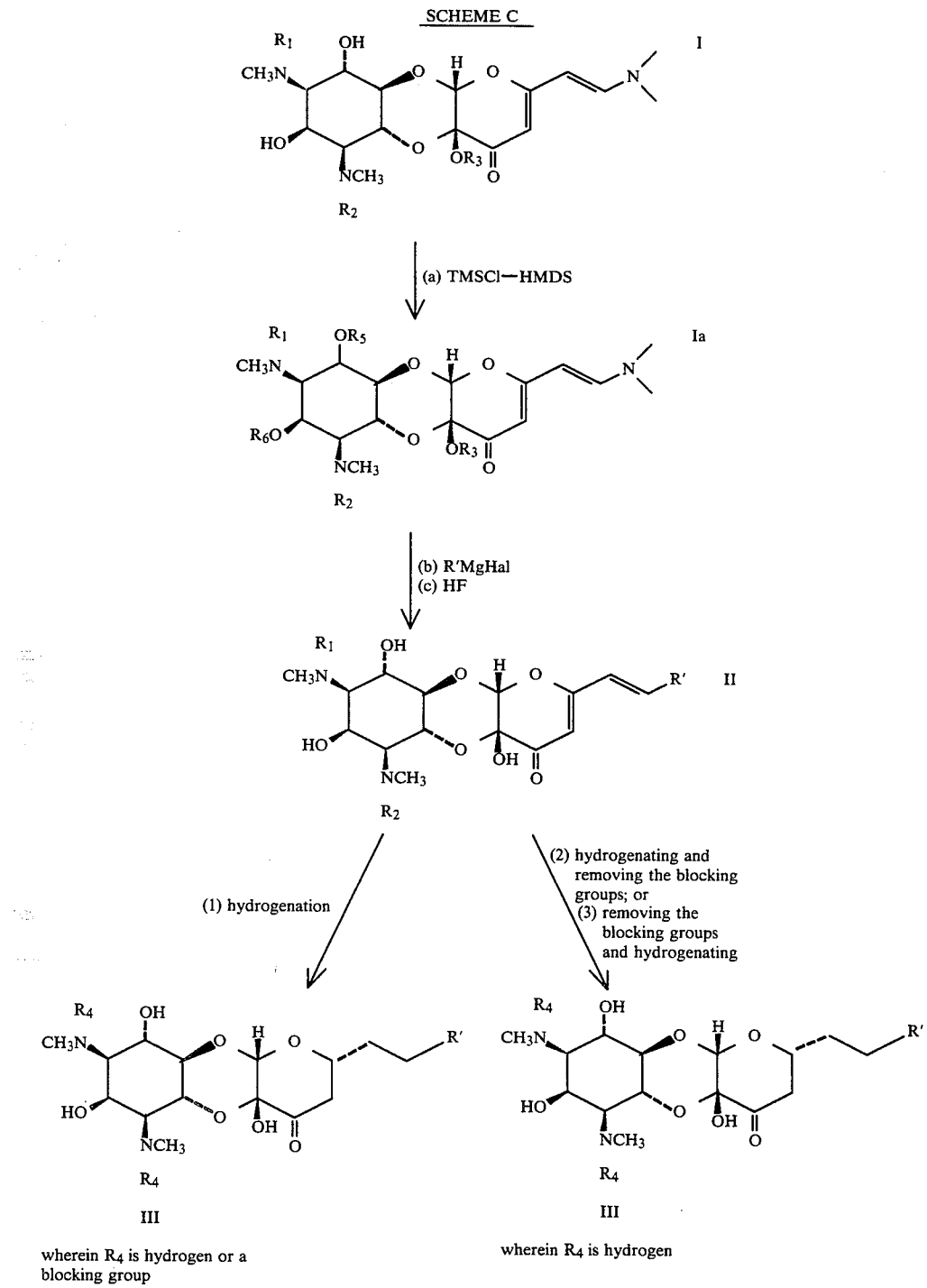
I claim:
1. A compound having the formula
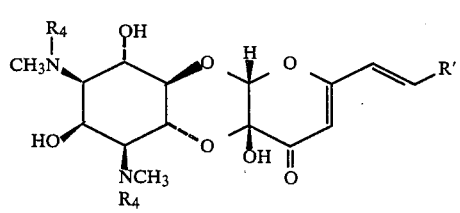
IIb
wherein $R_4$ is hydrogen or a blocking group; and
$R'$ is alkyl of from 1 to 18 carbon atoms, inclusive, with the proviso that when $R_4$ is hydrogen, $R'$ is alkyl of from 7 to 18 carbon atoms, inclusive.
2. A compound of claim 1 wherein $R_4$ is benzyloxycarbonyl and $R'$ is ethyl.
3. A process for preparing a compound having the formula

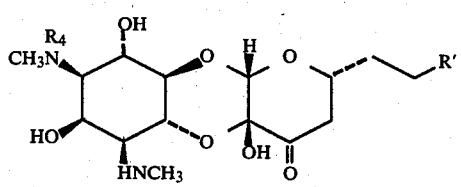

wherein R' is alkyl of from 1 to 18 carbon atoms, inclusive; and

R$_4$ is hydrogen or a blocking group; which comprises (1) hydrogenating in the presence of a palladium catalyst a compound having the formula

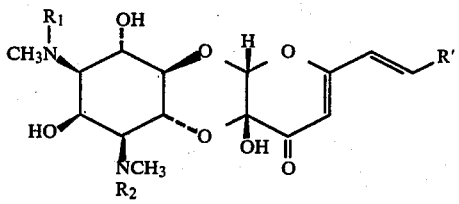

wherein R$_1$ and R$_2$ are blocking groups; and R' is as defined above to obtain the compound III with the proviso that R$_4$ is hydrogen if the blocking groups, R$_1$ and R$_2$ are removed by the hydrogenation and R$_4$ is a blocking group if the blocking groups R$_1$ and R$_2$ are not removed by the hydrogenation; or which comprises (2) hydrogenating in the presence of a palladium catalyst a compound having the formula

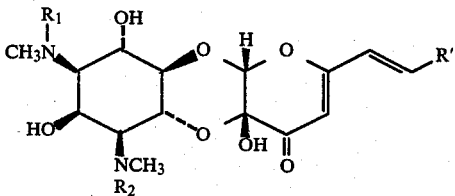

wherein R$_1$, R$_2$ and R' are as defined above with the proviso that R$_1$ and R$_2$ are blocking groups that are not removed by the hydrogenation and removing the blocking groups to obtain the compound III wherein R$_4$ is hydrogen.

4. A process according to claim 3 wherein R' is ethyl so that the embodiment is 6'-propyl spectinomycin.

5. A process according to claim 3 wherein R$_1$ and R$_2$ are benzyloxycarbonyl.

6. A process for preparing a compound having the formula

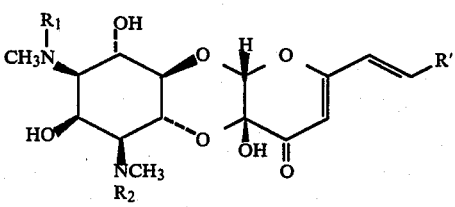

wherein R$_1$ and R$_2$ are the same and are a blocking group; and

R' is alkyl of from 1 to 18 carbon atoms, inclusive; which comprises (a) stirring an enamine having the formula

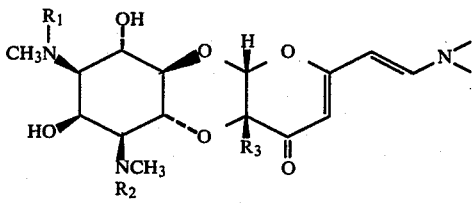

wherein R$_1$ and R$_2$ are as defined above; and
R$_3$ is acyl;
with a silylating reagent;

(b) treating the product of step (a) with a compound having the formula R' MgHal wherein Hal is bromo, chloro and iodo and R' is as defined above; and (c) adding a compound to remove the silicon containing protective group of the product of step (a) to obtain the compound II.

7. A process according to claim 6 wherein the silylating reagent compounds are a mixture of trimethylsilylchloride and hexamethyldisilazane.

8. A process according to claim 6 wherein R' is ethyl.

9. A process according to claim 6 wherein step (c) is accomplished by adding aqueous HF to the product of step (b).

10. A process for preparing a compound having the formula

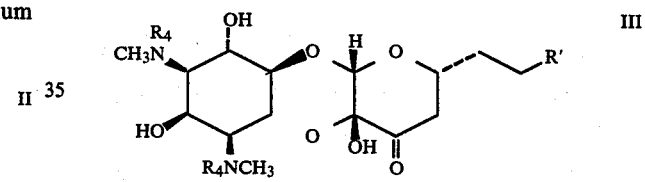

wherein R' is alkyl of from 1 to 18 carbon atoms, inclusive; and

R$_4$ is hydrogen or a blocking group which comprises (a) stirring an enamine having the formula

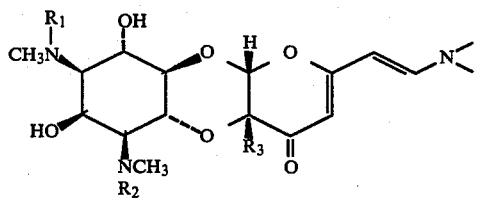

wherein R$_1$ and R$_2$ are the same and are a blocking group; and
R$_3$ is acyl;
with a silylating agent;

(b) treating the product of step (a) with a compound having the formula R' MgHal wherein R' is as defined above;

(c) adding a compound to remove the silicon containing protective group of the product of step (a); and (1) hydrogenating the compound of step (c) to obtain the compound III with the proviso that R$_4$ is hydrogen if the blocking groups R$_1$ and R$_2$ are removed by the hydrogenation and R$_4$ is a blocking group if the blocking groups R$_1$ and $R_2$ are not removed by the hydrogenation; or (2) hydrogenating the compound of step (c) to obtain the compound III with the proviso that $R_1$ and $R_2$ blocking groups that are not removed by the hydrogenation and removing the blocking groups to obtain the compound III wherein $R_4$ is hydrogen.

11. A process according to claim 10 wherein R' is ethyl.

12. A process according to claim 10 wherein the silylating reagent is a medium comprising hexamethyldisilazane and trimethylsilylchloride; the compound of step (2) having the formula R' MgHal is R' MgBr; the compound of step (3) which is added to remove the silicon containing protective groups is HF; and the hydrogenation of step (4) adds hydrogen to the product of step (3) in the presence of a paladium/$BaSO_4$ catalyst and $H_2SO_4$ is added for the acidification of step (4).

* * * * *

UNITED STATES PATENT OFFICE
CERTIFICATE OF CORRECTION

Patent No. 4,578,485        Dated March 25, 1986

Inventor(s) David R. White

It is certified that error appears in the above-identified patent and that said Letters Patent are hereby corrected as shown below:

Column 8, IIa, line 43 " 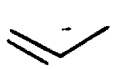 " should read -- 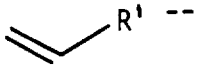 --

Column 8, II, line 61 " 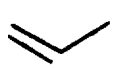 " should read -- 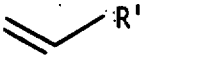 --

Column 9, III, line 3 "  " should read --  --

Column 9, Scheme A, III "  " should read -- 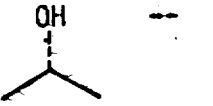 --

Signed and Sealed this

Eleventh Day of November, 1986

Attest:

DONALD J. QUIGG

Attesting Officer        Commissioner of Patents and Trademarks